United States Patent [19]

Francotte et al.

[11] Patent Number: 6,027,730
[45] Date of Patent: Feb. 22, 2000

[54] HERPES SIMPLEX VACCINE COMPRISING HSV GLYCOPROTEIN GD AND 3 DEACYLATED MONOPHOSPHORYL LIPID A

[75] Inventors: Myriam Francotte; Jean-Paul Prieels; Moncef Slaoui; Nathalie Marie-Josephe Claude Garcon-Johnson, all of Rixensart, Belgium

[73] Assignee: Smithkline Beecham Biologicals, Rixensart, Belgium

[21] Appl. No.: 08/303,542

[22] Filed: Sep. 9, 1994

Related U.S. Application Data

[63] Continuation of application No. 08/119,091, filed as application No. PCT/EP92/00592, Mar. 17, 1992, abandoned.

[30] Foreign Application Priority Data

Mar. 21, 1991 [GB] United Kingdom ................... 9105992

[51] Int. Cl.$^7$ ......................... A61K 39/245; A61K 45/00; A61K 9/16; A01N 59/06
[52] U.S. Cl. .................................... 424/229.1; 424/184.1; 424/229.1; 424/226.1; 424/192.1; 424/202.1; 424/282.1; 424/227.1; 424/231.1; 424/208.1; 424/690; 424/698; 424/486; 424/499; 514/12; 514/4; 514/8; 530/350
[58] Field of Search ............................. 424/184.1, 229.1, 424/226.1, 192.1, 202.1, 282.1, 227.1, 231.1, 208.1, 690, 698, 486, 499; 530/350; 514/12, 4, 8

[56] References Cited

U.S. PATENT DOCUMENTS

| | | |
|---|---|---|
| 4,372,945 | 2/1983 | Likhite . |
| 4,474,757 | 10/1984 | Arnon et al. . |
| 4,762,708 | 8/1988 | Cohen et al. . |
| 4,877,611 | 10/1989 | Cantrell . |
| 4,912,094 | 3/1990 | Myers et al. . |
| 5,110,587 | 5/1992 | Paolett et al. . |
| 5,149,529 | 9/1992 | Ho et al. . |
| 5,149,660 | 9/1992 | Cohen et al. . |
| 5,158,939 | 10/1992 | Takayama . |
| 5,166,173 | 11/1992 | Hwang et al. . |
| 5,171,568 | 12/1992 | Burke et al. . |
| 5,196,452 | 3/1993 | Hwang et al. . |
| 5,244,792 | 9/1993 | Burke et al. . |
| 5,334,379 | 8/1994 | Pillai et al. . |
| 5,470,718 | 11/1995 | O'Callaghan . |
| 5,554,372 | 9/1996 | Hunter . |
| 5,597,573 | 1/1997 | Kamireddy et al. . |
| 5,650,152 | 7/1997 | Anderson et al. . |
| 5,723,130 | 3/1998 | Hancock et al. . |
| 5,750,110 | 5/1998 | Prieels et al. . |
| 5,750,114 | 5/1998 | Burke et al. . |
| 5,776,468 | 7/1998 | Hauser et al. . |
| 5,795,579 | 8/1998 | Burke et al. . |

FOREIGN PATENT DOCUMENTS

| | | |
|---|---|---|
| 139417 | 5/1985 | European Pat. Off. . |
| 356340 | 2/1990 | European Pat. Off. . |
| 2220211 | 1/1990 | United Kingdom . |
| 8302897 | 9/1983 | WIPO . |
| WO 88/02634 | 4/1988 | WIPO . |
| WO9216231 | 10/1992 | WIPO . |
| WO9216556 | 10/1992 | WIPO . |
| WO8302897 | 1/1993 | WIPO . |
| WO9319780 | 10/1993 | WIPO . |
| WO9400153 | 1/1994 | WIPO . |
| WO9419013 | 9/1994 | WIPO . |

OTHER PUBLICATIONS

L. Sanchez–Pescador et al., A Comparison of Adjuvant Efficacy for a Recombinant Herpes Simplex Virus Glycoprotein Vaccine (1988), Tech. Advances in Vac. Develop., p. 455–469.
Lawrence R. Stanberry et al., Herpes Simplex Virus Glycoprotein Immunotherapy of Recurrent Gentil Herpes: Factors Influencing Efficacy, Antiviral Research 11, 1989, p. 203–214.
Rhoda Ashley et al., Humoral Immune Response to Herpes Simplex Virus Type 2 . . . , J. Virology 56, 1985, p. 475–481.
Kent R. Myers et al., A Critical Determinant of Lipid A Endotoxic Activity, pp. 145–156 in Excerpta Medic, 1990, Novotny et al. Eds.
Vogel et al. In: Vaccine Design ed. Powell et al pp. 2–92, 1994.
Bomford, Rev. in Medical Virology; 2:169–174, 1992.
Schultz et al Vaccine 13/5:503–508, 1995.
Sanchez–Pescador et al J. Immunology 141:1720–1727, 1988.
Schneerson et al, J. Immunology 147:2136–2140, 1991.
Long et al. Infect. Imm. 37(2):761–764, Feb. 1984.
Cremer et al. Vaccinia Viruses as Vectors For Vaccine Antigens. Ed:Quinnan pp. 153–161, 1985.
Ghiasi et al. Antiviral Research. 28:147–157, 1995.
Berman et al, Herpesvirus 21:637–49 UCLA Symp Mol. Cell. Biol, New Series, 1984.
Schneerson et al, J Immunol, 147(7):2316–40, Oct. 1991.
Drew et al, 1992, J. Gen. Virol. 73:2357–66.
Langenberg et al, 1995, Annals Internal Med. 122(12):889–898.
Hazama et al, 1993, Immunology 78:643–648.
Geerligs et al, 1989, J. Immunol. Methods, 124:95–102.
Sanchez–Pescader et al, 1988, J. Immunol. 141(5):1720–27.
Naylor et al, 1982, Inf. & Imm. 36(3):1209–1216.
Zarlings et al, 1986, J. Immunol., 136(12):4669–4673.
Eisenberg et al, 1985. J. Virol. 56(3):1014–17.
Berman et al, 1988, J Infect Dis. 157(5):897–902.
Lasky et al, 1984. Bio/Technology, 2/6:527–532.

(List continued on next page.)

*Primary Examiner*—Nita Minnifield
*Attorney, Agent, or Firm*—Zoltan Kerekes; Stephen Venetianer; Charles M. Kinzig

[57] ABSTRACT

Novel herpes simplex (HSV) vaccine formulations are provided. These comprise HSV glycoprotein gD or immunological fragments in conjunction with 3 Deacylated monophosphoryl lipid A.

11 Claims, 1 Drawing Sheet

OTHER PUBLICATIONS

Weis et al, 1983, Nature, 302(3):72–74.
Brynestad et al, 1990, J. Virol. 64(2):680–685.
Mertz et al, 1990, J. Infect. Dis. 161:653–660.
Stanberry et al, 1987, J. Infect. Dis. 155(5):914–920.
Plotkin et al, 1988. Vaccines, pp. 568–575. WB Saunders Co.
Burke, 1991, J. Inf. Dis. 13(Supp 11):S906–11.
Rooney et al, 1991, J. Infect. Dis. 13(Suppl 11):S898–903.
Pass. 1988. J. Am. Acad. Dermatol. 18:224–6.
Berman 1988. J. Am Acad Dermatol. 18:226–30.

HERPES SIMPLEX VACCINE COMPRISING HSV GLYCOPROTEIN GD AND 3 DEACYLATED MONOPHOSPHORYL LIPID A

CROSS-REFERENCES TO RELATED APPLICATIONS

This is a continuation of application Ser. No. 08/119,091, filed Dec. 6, 1993, now abandoned, which is a 371 of International Application Number PCT/EP92/00592, filed Mar. 17, 1992.

BACKGROUND OF THE INVENTION

1. Field of the Invention

The present invention relates to novel vaccine formulations, methods for preparing them and to their use in therapy. In particular, the present invention relates to novel formulations for treating Herpes Simplex Virus infections, more particularly Herpes Simplex virus 2(HSV-2) infections.

2. Description of the Prior Art

HSV-2 is the primary etiological agent of herpes genitalis and together with HSV-1 (the causative agent of herpes labialis) are characterised by their ability to induce both acute diseases and to establish a latent infection, primarily in neuronal ganglia cells.

Genital herpes is estimated to occur in about 5 million people in the U.S.A. alone with 500,000 clinical cases recorded every year (primary and recurrent infection). Primary infection typically occurs after puberty and is characterised by the localised appearance of painful skin lesions, which persist for a period of between 2 to 3 weeks. Within the following six months after primary infection 50% of patients will experience a recurrence of the disease. About 25% of patients may experience between 10–15 recurrent episodes of the disease each year. In immunocompromised patients the incidence of high frequence recurrence is statistically higher than in the normal patient population.

Both HSV-1 and HSV-2 virus have a number of glycoprotein components located on the surface of the virus. These are known as gA, gB, gC, gD and gE etc.

Glycoprotein D is located on the viral membrane, and is also found in the cytoplasm of infected cells (Eisenberg R. J. et al; J of Virol 1980 35 428–435). It comprises 393 amino acids including a signal peptide and has a molecular weight of approximately 60 kD. Of all the HSV envelope glycoproteins this is probably the best characterised (Cohen et al J. Virology 60 157–166). In vivo it is known to play a central role in viral attachment to cell membranes. Moreover, glycoprotein D has been shown to be able to elicit neutralising antibodies in vivo (Eing et al J. Med. Virology 127: 59–65). However, latent HSV-2 virus can still be reactivated and induce recurrence of the disease despite the presence of high neutralising antibodies titre in the patients sera.

The ability to induce neutralising antibody alone is insufficient to adequately control the disease. In order to prevent recurrence of the disease, any vaccine will need to stimulate not only neutralising antibody, but also cellular immunity mediated through T-cells. The present invention achieves these aims.

SUMMARY OF THE INVENTION

The present invention provides a vaccine comprising HSV glycoprotein D or an immunological fragment thereof in conjunction with 3-o-deacylated monophosphoryl lipid A (3D-MPL) a deacylated derivative of monophosphoryl lipid A, and a suitable carrier. Typically the glycoprotein D will be from HSV-2. The carrier may be an oil in water emulsion, or alum, 3D-MPL will be present in the range of 10 $\mu$g–100 $\mu$g preferably 25–50 $\mu$g per dose wherein the antigen will typically be present in a range 2–50 $\mu$g per dose.

3D-MPL may be obtained according to the methods described in U.S. Pat. No. 4,912,094 (Ribi).

BRIEF DESCRIPTION OF THE DRAWING

FIG. 1 shows the results of vaccinations with formulations of rgD$_2$t and 3D-MPL in an oil in water emulsion; rgD$_2$t; 3D-MPL and alum; and rgD$_2$t in alum, and compares such results to an untreated control group.

DESCRIPTION OF THE PREFERRED EMBODIMENTS

Figure 1:
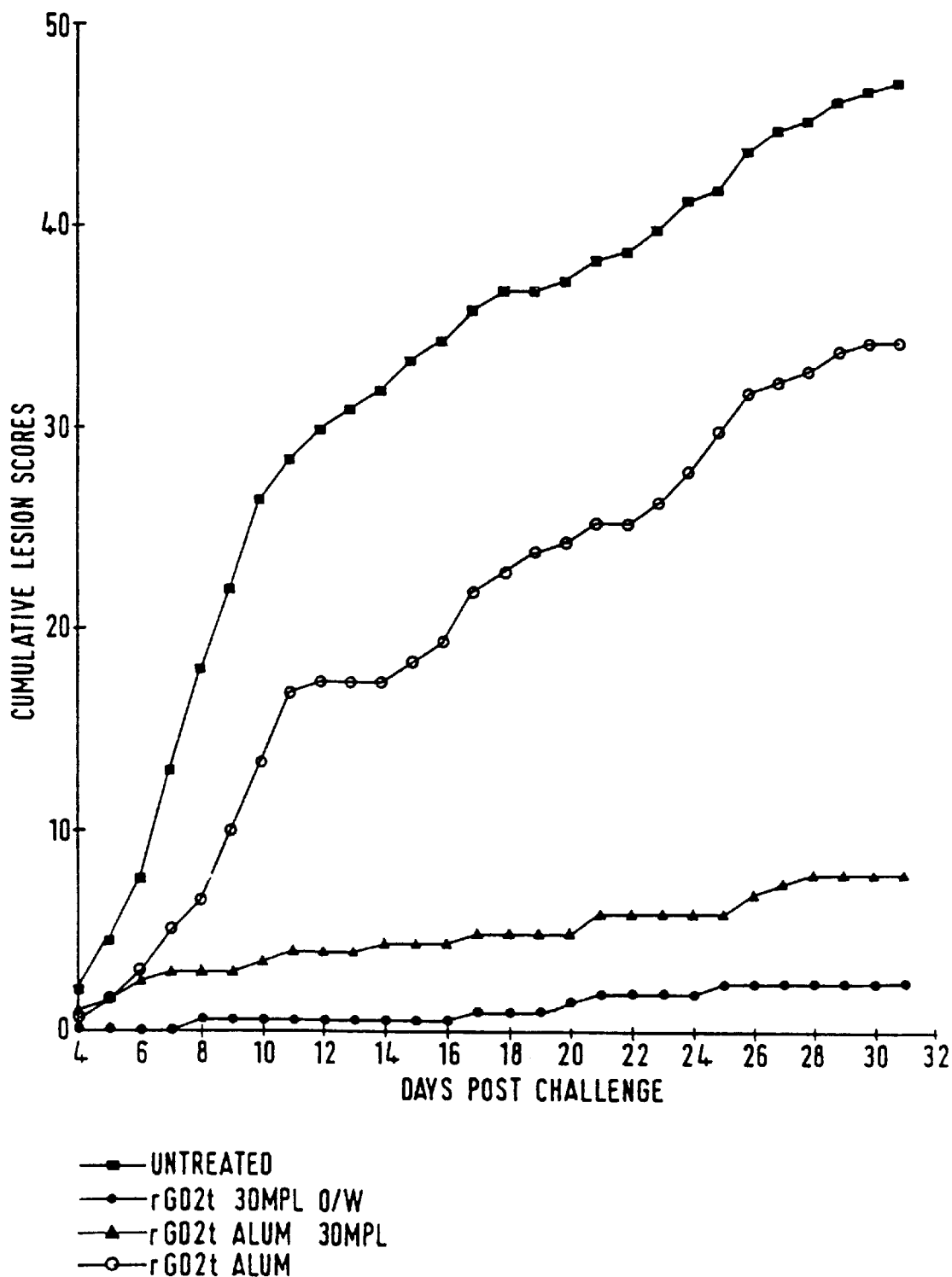
FIG. 1 depicts the effects of vaccination on recurrent Herpes Simplex Virus disease. Specifically.

An embodiment of the invention is a truncated HSV-2 glycoprotein D of 308 amino acids which comprises amino acids 1 through 306 naturally occuring glycoprotein with the addition Asparagine and Glutamine at the C terminal end of the truncated protein devoid of its membrane anchor region. This form of the protein includes the signal peptide which is cleaved to yield a mature 283 amino acid protein. The production of such a protein in Chinese Hamster ovary cells is well known in the art, see for example Genentech's European patent EP-B-139 417.

The mature truncate preferably is used in the vaccine formulations of the present invention as is designated rgD$_2$t.

The HSV antigen may be chemically or otherwise conjugated to a particulate carrier. A particularly preferred approach is to chemically conjugate to particulate Hepatitis B surface antigen through free sulfilydryl groups located on the surface of the Hepatitis B surface antigen. The covalent coupling of glycoprotein D of HSV-2 to a particulate carrier is described in U.K. Patent Application No. 9027623.9 as follows:

Covalent coupling of the glycoprotein D of Herpes Simplex 2 Virus to a particulate carrier Introduction The glycoprotein D of HSV 2 (gD$_2$t) expressed in CHO cells (Lasky and Dowbenko DNA, 1984, 3(1), 23–29) is covalently coupled to a recombinant HBsAg particle containing free SH groups.

Materials and Methods a. Agents 5,5'Dithiobis 2-nitrobenzoic acid (Ellman's reagent or DTNB) and N-succinimidyl(4-iodoacetyl)- aminobenzoate (SIAB) were purchased from PIERCE.

2,4,6-Trinitrobenzenesulfonic acid (TNBS) was obtained from SERVA.

Recombinant gD$_2$t was expressed in CHO cells and purified by SmithKline Biologicals.

gD$_2$t was iodinated by the enzymobeads method of PIERCE.

HBsAg particles were produced by SmithKline Biologicals.

b. Methods b. 1. Characterization of gD$_2$t b. 1.1 Quantitative determination of sulfhydryl groups:

To 150 ml of gD$_2$t (23 mM in Na$_2$HPO$_4$0.02 M pH 7) 1 ml of DTNB (3.28 mM in Na$_2$HPO$_4$0.04 M pH 8) is added.

After 5 min, the optical density at 412 nm is determined against a blank lacking protein. An extinction coefficient of $1.3 \times 10^4 M^{-1} cm^{-1}$ is used to calculate the concentration of sulfhydryl groups reacting (Ellman, *Arch. Biochem. Biophys.*, 1959, 82, 70).

b. 1.2 Quantitative determination of lysine residues:

50 ml of TNBS/$H_2O$ 24.5 mM are added to 50 ml of $gD_2t$ (58 mM in $Na_2HPO_4$ 0.02 M pH 7) diluted in 200 ml of borate buffer (0.05 M $Na_2B_4O_7$ adjusted to pH 9.5 with 0.05 M NaOH).

After 3 hours in the dark at room temperature the change in absorbance at 367 nm is followed against a blank without protein.

The extent of trinitrophenylation is calculated on the basis of an $e_{367}$ nm=$1.1 \times 10^4$ $M^{-1}cm^{-1}$ (Plapp et al., *J. Biol. Chem.* 1971, 246 (4), 939–945).

b.2. Activation of $gD_2t$ with SIAB 100 ml of $gD_2t$ (23 mM in $Na_2HPO_4$ 0.02 M pH 7)+100 ml $gD_2t$ $I^{125}$ are incubated for 30 min at 37° C. with 2 ml SIAB (25 mM in DMSO) which corresponds to a molar ratio succinimide/lysine of 2. The excess of cross-linker is eliminated by dialysis (2 hours against $Na_2HPO_4$ 0.02 M pH 8) and the reaction mixture is concentrated to 100 ml by ultrafiltration on an YM 10 centricon.

b.3. Coupling to HBsAg particle $gD_2t$ (100 ml), concentrated (1 mg/ml) and SIAB-activated, is incubated with 53 ml of HBsAg particles (1 mg/ml in $Na_2HPO_4$ 10 mM pH 7.2, NaCl 150 mM) for various times at 37° C.

The initial molar ratio $gD_2$/S monomer is 1/1.

The particulate $gD_2t$ is purified by a 1.5 M CsCl gradient (45 hours, 65000 rpm in a 70.1 Ti rotor).

b.4. Quantification of $gD_2t$ coupled per particle 50 ml of water are added to a vial of enzymobeads. After one hour, 50 ml of $Na_2HPO_4$ 0.2 M pH 7.2, 25 ml $gD_2t$ (1 mg/ml), 0.5 mCi $NaI^{125}$ (Amersham) and 25 ml 1% b-D-Glucose are added.

After 20 min at room temperature, the reaction is completed and the iodinated protein is separated from free iodine by chromatography on DOWEX Ag 1×8 resin saturated by BSA 1%.

The specific activity of the $gD_2t$ involved in the coupling may be determined by the radioactivity detected in the mixture of labeled and non-labeled $gD_2t$. The amount of $gD_2t$ coupled to particles may be determined by this specific activity.

a. Characterization of $gD_2t$ a. 1. Quantitative determination of sulfhydryl groups No free thiol is detected on the $gD_2t$ by DTNB. This result fits the aminoacid sequence of the protein. The truncated $gD_2t$ molecule used (283 aa) contains 6 cysteine residues, each involved in disulfide bridges that constitute discontinuous epitopes. Therefore, $gD_2t$ is an ideal molecule for the activation step with a heterobifunctional cross-linker without risk of homopolymerisation.

a.2. Quantitative determination of lysine residues

The number of free amino groups are detected by TNBS either on the native or on the SIAB activated $gD_2t$. The number of free lysines decreases as a function of the excess of SIAB.

With a molar ratio SIAB/lysine of 2, four residues are activated.

The number of detected lysines on the native protein (10) is close to the number determined in the amino acid sequence (11).

b. Activation of $gD_2t$ by SIAB

After an activation of 30 min at 37° C. with a molar ratio of SIAB/lysine of 2, the absence of homopolymers of $gD_2t$ is checked by gel filtration.

On a TSK 3000 column, the homopolymers elute in the void volume (8 min) and the monomeric $gD_2t$ has a retention time of 15 min.

Despite the absence of cysteine residues in the protein, formation of homopolymers is observed when $gD_2t$ is activated at a concentration of 2.5 mg/ml. An aspecific reactivity of the halogen in SIAB for lysine, methionine or histidine residues may explain this phenomenon (see Means and Feeney, Chemical Modifications of Proteins; Holden Day publ., 1971, page 107).

Initial protein concentration is a decisive factor in homopolymerisation events. If $gD_2t$ is activated at a concentration of 0.5 mg/ml, the formation of homopolymers decreases from 50 to 10%.

c. Coupling to HBsAg particle

The HBsAg-$gD_2t$ conjugate obtained after a 30 min, 2 hrs or over night incubation at 37° C. is purified by CsCl gradient. The $gD_2t$ homopolymers have a different density to the carrier and do not contaminate the conjugate. The yield of coupling increases with time as shown in Table 2. 0.2 $gD_2t$ molecules are coupled per S monomer (twenty per particle) as calculated by radioactivity detected in the particle's density area.

Influence of incubation on the yield of coupling:

| Time   | $gD_2t$/S monomer |
| ------ | ----------------- |
| 30 min | 0.08              |
| 2 hrs  | 0.14              |
| 15 hrs | 0.20              |

The formulations of the present invention are very effective in inducing protective immunity, even with very low doses of antigen (e.g. as low as 5 µg $rgD_2t$).

They provide excellent protection against primary infection and stimulate, advantageously both specific humoral (neutralising antibodies) and also effector cell mediated (DTH) immune responses.

Non-toxic oil in water emulsions preferably contain a non-toxic oil, e.g. squalane or squalene, a emulsifier, e.g. Tween 80, in an aqueous carrier. The aqueous carrier may be for example, phosphate buffered saline.

The present invention in a further aspect provides a vaccine formulation as herein described for use in medical therapy, particularly for use in the treatment or prophylaxis of Herpes Simplex viral infections.

The vaccine of the present invention will contain an immunoprotective quantity of HSV gD or immunological fragment thereof and this maybe prepared by conventional techniques.

Vaccine preparation is generally described in New Trends and Developments in Vaccines, edited by Voller et al., University Park Press, Baltimore, Md., U.S.A 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

The amount of protein in each vaccine dose is selected as an amount which induces an immunoprotective response without significant, adverse side effects in typical vaccinees. Such amount will vary depending upon which specific immunogen is employed. Generally, it is expected that each dose will comprise 1–1000 µg of protein, preferably 2–100 µg, most preferably 4–40 µg. An optimal amount for a particular vaccine can be ascertained by standard studies involving observation of antibody titres and other responses in subjects. Following an initial vaccination, subjects may receive a boost in about 4 weeks.

In addition to vaccination of persons susceptible to HSV infections, the pharmaceutical compositions of the present invention may be used to treat, immunotherapeutically, patients suffering from HSV infections.

In a further aspect of the present invention there is provided a method of manufacture as herein described, wherein the method comprises mixing HSV-2 glycoprotein D or an immunological fragment with a carrier, e.g. an oil in water emulsion or alum, and 3D-MPL.

Comprison of Adjuvant Efficacy of a Recombinant Herpes Simpex Virus Glycoprotein D Subunit Vaccine In this study, the ability of several adjuvants to improve the protective immunity of a recombinant glycoprotein D from Herpes Simplex Virus (HSV) type 2 ($rgD_2t$) was evaluated in a guinea pig model. Adjuvants tested were aluminium hydroxide, aluminium hydroxide in combination with 3 Deacyl-Monophosphoryl Lipid A, and 3 Deacyl-Monophosphoryl Lipid A delivered in an oil in water emulsion.

1. Description of the Antigen

As it is well known in the art, HSV $rgD_2t$ is a genetically engineered recombinant truncated glycoprotein produced in transfected Chinese hamster ovary (CHO) cells (see for example European Patent No. 0189417).

2. Anitgen-Adjuvant Preparations and Immunization Schedules

Two separate experiments were performed to evaluate the protective immunity of several $rgD_2t$ formulations in the guinea pig model. In the first experiment, groups of guinea pigs were immunized three times with a low antigen dose (5 μg of $rgD_2t$) in 4 adjuvant formulations prepared as described below. Two weeks after the last immunization, they were challenged intravaginally with HSV type 2 and were monitored daily for the development of primary and recurrent HSV2 disease. In the second experiment, these formulations were further evaluated on larger animal groups. Factors influencing efficacy of these formulations were also tested such as antigen dose and adjuvant composition.

2.1. Antigen-Adjuvant Preparations

In the first experiment, guinea pigs were immunized with the following adjuvant preparations. Each dose (5 μg) was administered in a 0.25 ml volume.

2.1.1. rgD2t/Alum(Aluminium Hydroxide)

Alum was obtained from Superfos (Alhydrogel, (Boehimte) Superfos, Denmark). Five μg of purified $rgD_2t$ was adsorbed overnight at 4° C. on aluminium hydroxide (alum) corresponding to 0.25 mg equivalents $Al^{3+}$ in 0.25 ml of 150 mM NaCl 10 mM phosphate buffer pH 6.8.

2.1.2. gD2t/Aluminium Hyroxidie plus 3D-MPL

3D-MPL was obtained from Ribi Immunochem Research, Inc. After an overnight adsorption of 5 μg $gD_2t$ on alum as described in 2.1.1., the adjuvant preparation was centrifuged and its supernatant removed. An equal volume of adsorption buffer containing 100 μg 3D-MPL was then added to the alum-bound $rgD_2t$.

For both $rgD_2t$/Alum preparations, more than 98% of the $rgD_2t$ was found to be incorporated in aluminium hydroxide adjuvant.

2.1.3. rgD2t/3D-MPL in an Oil in Water Emulsion (R)

The oil in water emulsion was prepared using 12% w/v lecithin added to Squalene oil and 0.08% Tween 80. 3D-MPL was added at a concentration 100 fold higher than the final desired concentration. 1% of this preparation was then mixed in a 0.25 ml volume to 5 μg $rgD_2t$ in aqueous phase, yielding a 1% oil in water emulsion containing 100 μg 3D-MPL.

Similar adjuvant formulations prepared as above but containing different amounts of $rgD_2t$ and/or immunostimulator were used in the second experiment. They were administered in a total volume of 0.5 ml. These formulations are described below.

$rgD_2t$/Alum: Five or 20 μg $rgD_2t$; 0.5 mg equivalents $Al^{3+}$ per 0.5 ml dose.

rgD2t/Alum plus 3D-MPL: Five or 20 μg $rgD_2t$; 0.5 mg equivalents $Al^{3+}$; 50 μg 3D-MPL per 0.5 ml dose.

rgD2t/3D-MPL in o/w emulsion (R): Five or 20 μg $rgD_2t$ were formulated in an 1% o/w emulsion as described above (2.1.3). A 0.5 ml dose contained 5 μg or 20 μg $rgD_2t$, 50 μg 3D-MPL in a 1% o/w emulsion.

rgD2t/3D-MPL in o/w emulsion (S): The vehicle was prepared as follows: To phosphate buffered saline (PBS) containing 0.4% (v/v) Tween 80 are added 5% (v/v) Pluronic L121 and 10% squalane and the resulting mixture microfluidized ten times through a microfluidizer (Model M/110 Microfluidics Corp.,) such that the resulting emulsion comprises only submicron particles. 50 μg of 3D-MPL was then added to the emulsion. One volume of this emulsion, containing 3D-MPL was mixed with an equal volume of twice concentrated antigen and vortexed briefly to ensure complete mixing of the components. The final preparation consisted of 0.2% Tween 80, 2.5% Pluronic L121, 5% Squalane, 50 μg 3D-Mpl and 5 μg or 20 μg rgD2t in a 0.5 ml dose.

2.2. Immunization Schedule

Groups of female Hartley guinea pigs (200–250 gr) were immunized three times at day 0, 28 and 95 with 5 μg $rgD_2t$ formulated in 4 different adjuvant formulations.

Immunizations were done subcutaneously with injection volume of 0.25 ml. Control animals were injected according to the same protocol with adjuvant alone or were untreated.

The different groups were immunized as follows:

Group 1 (n=4): 5 μg $rgD_2t$/3D-MPL (100 μg) in o/w emulsion (R)

Group 2 (n=4): 5 μg $rgD_2t$/Alum plus 3D-MPL (100 μg)

Group 3 (n=4): 5 μg $rgD_2t$/Alum

Group 4 (n=5): Alum alone

Group 5 (n=5): 3D-MPL (100 μg) alone

Group 6 (n=8): untreated

Animals were bled every 2 weeks for antibody determinations by ELISA and neutralization assays as described below.

The different formulations were also tested for their ability to induce T cell mediated immunity, as measured by the induction of delayed-type hypersensitivity responses. The read-outs applied for evaluation of the humoral and cellular immune responses induced by the different $rgD_2t$ formulations are described below.

In order to compare the protective immunity induced by the $rgD_2t$ formulations, all the guinea pigs were challenged intravaginally with $10^5$ plaque-forming units (pfu) of HSV2, strain MS, 2 weeks after the last immunization. They were monitored daily for clinical signs of acute infection as well as for evidence of recurrent herpetic diseases. Vaginal swab samples were collected on day 5 after viral challenge and titered for infectious virus.

A detailed description of the guinea pig intravaginal model is given below.

In the second experiment, the immunogenicity of the following $rgD_2t$ formulations was evaluated in larger animal groups. Two antigen doses were compared (5 and 20 μg) and different adjuvant composition were tested. A dose of 50 μg 3 DMPL was used and its effects compared to the 100 μg dose previously used.

Groups of female Hartley guinea pigs were immunized three times at days 1, 28 and 84, as follows:

Group I (n=8): 20 μg rgD$_2$t/3DMPL (50 μg) o/w emulsion (R)

Group II (n=8): 5 μg rgD$_2$t/3DMPL (50 μg) o/w emulsion (R)

Group III (n=10): 20 μg rgD$_2$t/3DMPL (50 μg) o/w emulsion (S)

Group IV (n=10): 5 μg rgD$_2$t/3DMPL (50 μg) o/w emulsion (S)

Group V (n=10): 20 μg rgD$_2$t/Alum+3DMPL (50 μg)

Group VI (n=10): 5 μg rgD$_2$t/Alum+3DMPL (50 μg)

Group VII (n=4): Alum+3DMPL (50 μg) alone

Group VIII (n=4): 3DMPL (50 μg) o/w emulsion (R) alone

Group IX (n=8): untreated

Immunizations were given in a 0.5 ml dose. Control groups were immunized according to the same protocol with adjuvant alone (Groups VII and VII) or were intreated (Group IX).

A last group (Group X) was immunized with a gD$_2$t Alum+3D-MPL formulation containing 100 μg 3D-MPL in a 0.25 ml dose, according to the protocol described in the first prophylactic experiment:

Group X (n=10): 5 μg rgD$_2$t/Alum plus 3DMPL (100 mg).

Animals were bled every two weeks for individual antibody determinations by ELISA and neutralization assays, as described below. Vaginal washings were collected after the second immunization and were assayed for the presence of systemic antibodies specific for gD$_2$t (anti-gD$_2$t antibodies of IgG class). Guinea pigs were challenged intravaginally with 105 pfu HSV2 (strain MS) 2 weeks after the last immunization. After challenge, they were monitored daily for clinical signs of acute infection (days 4 to 12 post challenge) as well as for evidence of recurrent herpetic disease (days 13 to 39 post challenge).

3. Read-outs

Several read-outs were set up to evaluate the specific antibody and cell mediated responses induced by vaccination with rgD$_2$t formulations. The protective value of these formulations was assessed in the guinea pig intravaginal model.

3.1. ELISA

An ELISA was designed to detect and quantify gD-specific antibodies in guinea pig sera and vaginal washings, using rgD$_2$t as the coating antigen.

3.1.1. Detection of IgG Antibodies Specific for rgD2t in sera

Antigen and antibody solutions were used at 50 μl per well. Antigen was diluted to a final concentration of 1 μg/ml in PBS and was adsorbed overnight at 4° C. to the wells of 96 wells microtitre plate (Maxisorp Immuno-plate, Nunc, Denmark). The wells were then washed 5 times with PBS Tween 0.1% (wash buffer) and incubated for 1 hour at 37° C. with PBS containing 1% bovine serum albumin, 4% newborn calf serum and 0.1% Tween (saturation buffer). Three-fold dilutions of sera (starting at 1/100 dilution) in the saturation buffer were added to the rgD$_2$t-coated wells and incubated for 2 hrs at room temperature. The plates were washed as above and biotin-conjugated sheep anti-guinea pig IgG (IgG1 and IgG2 specific, Serotec, Sopar Biochem., Belgium) diluted 1/3000 in saturation buffer was added to each well and incubated for 1 h.30 min. at 37° C. After a washing step, streptavidin-biotinylated peroxidase complex (Amersham, UK) diluted 1/1000 in saturation buffer was added and incubated for 30 min. at 37° C. Plates were washed as above and incubated with a solution of o-phenylenediaiine (Sigma) 0.04% H$_2$O$_2$0.03% in 0.1 M citrate buffer at pH 4.5.

Color reaction was stopped after 15 min by the addition of H$_2$SO$_4$ 2 M and the absorbance was readed at 492 nm.

ELISA titer was defined as the reciprocal of serum dilution which produced an absorbance (optical density measured at 492 nm equal to 50% of the maximal absorbance value (midpoint titer).

ELISA titers were calculated by a 4 parameter linear regression analysis using a computer program.

3.1.2. Detection of IgG Antibodies Specific for rgD2t in Vaginal Washings

Vaginal washings were first calibrated for their total IgG content by ELISA as follows. Maxisorp Immuno-plates were coated overnight at 4° C. with 1 μg/ml (50 μl per well) of purified goat anti-guinea pig IgG (Sigma, Belgium) diluted in PBS. The plates were washed and incubated with saturation buffer as above. Vaginal washings were diluted serially with two-fold dilutions (starting at a 1/100 dilution) in the saturation buffer and added to the plates. A standard curve of purified guinea pig IgG (Sigma, Belgium) was included (two fold dilution starting at a 100 ng/ml concentration) in each plate.

After a 2 hrs incubation at room temperature, the plates were washed as above and biotin-conjugated sheep antibodies specific for guinea pig IgG1 and IgG2 (Serotec, Sopar Biochem, Belgium) diluted 1/1000 in saturation buffer was added to each well and incubated for 1 h 30 min at 37° C. Next steps (addition of streptavidin-biotinylated peroxidase complex and color revelation) were as described above (3.1.1.).

The concentration of total IgG present in the vaginal washings was determined from the IgG standard curve, by a 4 parameters monlinear regression analysis using a computer program.

After calibration of their total IgG content, vaginal washings were tested for the presence of IgG antibodies specific for rgD$_2$t using the same ELISA as described for anti-gD antibody sera quantifications. Results were expressed as optical densities measured at 492 nm per 0.5 μg/ml total IgG.

3.2. Neutralization Assay

A 96 well format neutralization assay was set up as follows:

Serial two-fold dilutions of the samples to be tested were prepared directly in the 96 W plates (25 ul/well of each serum dilutions, duplicates). Fifty microliters of a mixture containing 4000 pfu of virus HG52 and complement (1/100 final dilution in the well) were added to each well. The plates were incubated for 1 hour at 37° C. One hundred microliters of BHK 21 cell suspension at $4.10^5$ cells/ml were then added to each well ($4.10^4$ cells/well). The plates were centrifuged for 5 minutes at 1000 rpm and incubated for five days at 37° C. in the presence of 7% CO$_2$.

After this period, the culture medium was gently removed and 100 μl of a solution of cristal violet (10% methanol, 90% H$_2$O, 0.3% cristal violet) were added to each well and incubated for 20 min. at room temperature. The plates were then abundantly washed with tapwater. The presence of plaques can easily be monitored by microscopic examination.

The neutralizing titer was defined as the reciprocal of the highest serum dilution at which no viral plaque was observed (100% protection of cytopathogen effect). It is important to note that at this time point, a complete cytopathogen effect (100% lysis of the cell monolayer) was observed in the control wells.

3.3. Delay-Type Hypersensitivity (DTH)

The different $rgD_2t$ formulations were also tested for their ability to induce a T cell specific immune response as measured by the induction of delayed-type hypersensitivity responses.

The adjuvant formulations prepared for the first experiment were used in this study. These preparations contained 5 µg of $rgD_2t$ per 0.25 ml dose. The immunization schedule was as follows: primary immunization: 0.25 ml of vaccine formulation given intramuscularly; booster immunization: 0.25 ml of vaccine formulation given intramuscularly 21 days later; skin test: 5 µg $rgD_2t$ given intradermally (in saline) 8 days later. All guinea pigs were skin tested with saline as control.

In addition, control guinea pigs (non immunized animals) were skin tested with $rgD_2t$. Erythema and induration at site of intradermal injection were monitored 24 and 48 hrs later.

3.4. Guinea-pig Intravaginal Model

The guinea pig model for HSV genital infection has been described by L R Stanberry et al (J. of Infectious Diseases 1982, 146:397–403; Intervirology 1985, 24:226–231).

Briefly, 2 weeks after the last immunization, the guinea pigs were challenged with $10^5$ pfu of HSV2 strain MS by intravaginal instillation. The clinical course of the primary infection was monitored by daily observation of the incidence and severity of external genital skin lesions during the 12-day post-challenge period.

Vaginal swabs were collected on day 5 after viral challenge and titered for infectious HSV2 by plaque assay, as described below. Animals were then examined daily for evidence of recurrent herpetic lesions from days 13 to 60. The herpetic lesions on the external genital skin were quantitated by using a lesion score scale ranging from 0 to 4(0=no lesion or redness; 0.5=redness; 1=vesicle; 1.5=≧4 small vesicles; 2=larger vesicles; 2.5=several large vesicles resulting from the fusion of vesicles as in score 2;3=size and number of vesicles increase; 3.5=lesions covering all the surface of the genital skin; 4=ulcerated lesions with maceration).

The degree of protection provided by the different $rgD_2t$ vaccines was evaluated according to the criteria defined below.

Protection Against Primary Disease (Days 0–12)

The animal was considered to be not protected if the following lesions were recorded:
   more than one red area at any time,
   one red area persisting in the same area for at least 3 successive days (0.5 lesion score),
   one or several vesicles (≧1 lesion score).

Protection Against Recurrent Disease (Days 13–60)

The animal was scored positive for recurrent disease either if a 0.5 lesion score was recorded for 2 successive days at least or if a lesion score ≧1 was observed at any day. An episode of recurrent disease was preceded and followed by a day without any lesions or redness.

The lesion severity for an animal is calculated as the sum of the scores measured during the primary infection (days 1–12). The lesion incidence represents the number of animals showing a lesion of >1 during the observation period (days 1–12 [primary disease] or days 13–60 [recurrent diseases]).

3.5. Virus Titration in Vaginal Swabs

Vaginal swabs were collected at day 5 after viral challenge. The vaginal vault was swabbed with a calcium alginate tipped swab premoistened in Basal Eagle's medium supplemented with 2% fetal calf serum, 2 mM L glutamine, 100 U/ml penicillin, 100 µg/ml streptomycin, 100 µg/ml gentamycin and 1 µg/ml amphotericin B (swab medium).

Each swab was broken and put into a sterile 12×75 mm 5 ml polyallomer tube containing 1 ml of swab medium. The tubes were then vortexed in order to take the virus out and frozen until use. For the titration itself, 6 wells culture plates containing $5.10^5$ cells/well were incubated overnight at 37° C. The tubes were thawed and serial dilutions of the samples in swab medium were prepared. After removal of the culture medium in the 6 wells, 200 µl of each samples dilution were transferred in duplicate on the cell monolayers and kept for one hour at 37° C. Four ml of a culture medium containing 1.5% carboxymethylcellulose were added to each well. The plates were then incubated for 2 days at 37° C. After this incubation period, the medium was gently removed and 1 ml of a solution of cristal violet (10% methanol, 90% $H_2O$, 0.3% cristal violet) was added to each well for 15 min. The plates were then thoroughly rinsed and the plaques were counted. HSV2 titer was expressed in pfu/ml.

4. Results

In a first set of experiments, groups of guinea pigs were immunized with a low antigen dose (5 µg $rgD_2t$) formulated in 4 different formulations. This suboptimal antigen dose was chosen in order to select the more potent $rgD_2t$ adjuvant combination that could provide protection against primary and recurrent HSV disease when administered to guinea pigs prior to intravaginal HSV2 inoculation (prophylactic trials).

4.1. Induction of Humoral Immunity

As shown in Table 1, groups vaccinated with $rgD_2t$ formulations containing 3D-MPL as immunostimulant showed higher ELISA and neutralizing titers in their sera than the group immunized with the $rgD_2t$/Alum vaccine. Good mean neutralizing titers were induced after 3 immunizations with $rgD_2t$ 3D-MPL o/w (R) or $rgD_2t$ Alum 3D-MPL.

4.2. Induction of Effector T Cell Response (DTH)

Skin test results (Table 2) showed that $rgD_2t$ formulated in 3D-MPL o/w emulsion induced the strongest DTH response. A specific DTH response was also induced by $rgD_2t$ Alum 3D-MPL. Similar experiments conducted in mice also revealed that $rgD_2t$ combined with Alum plus 3D-MPL was very potent in inducing an in vivo effector T cell response, in contrast to $rgD_2t$ Alum formulation.

4.3. Effect of Vaccination on HSV Primary Disease

Two weeks after the third immunization, guinea pigs were challenged intravaginally with HSV2. The effect of vaccination on the clinical and virological course of primary HSV2 infection is illustrated in FIG. 1 and summarized in Table 3. As compared to the control groups (Groups 4 to 6) that became infected and experienced acute primary disease, 100% of the animals vaccinated with the $rgD_2t$ 3D-MPL o/w formulation showed no evidence of herpetic disease, as monitored by skin lesion incidence and severity. Moreover, these animals did not show any viral replication in the vaginal tract as determined by vaginal virus titration at day 5 post challenge. Very similar results were obtained in the group vaccinated with $rgD_2t$/Alum 3D-MPL. This group never developed herpetic vesicles during the observation period (lesion score<1). Moreover, very low viral replication could be detected in the vaginal swabs collected. In contrast animals $rgD_2t$ adsorbed on alum were poorly protected (75% skin lesion incident).

4.4. Effect of Vaccination on HSV Recurrent Disease

Results are illustrated in FIG. 1 and summarized in Table 4.

Vaccination with rgD$_2$t formulations containing 3D-MPL (Groups 1 and 2) significantly altered the development of recurrent herpetic diseases. Two groups had significantly fewer recurrent episodes and recurrent day numbers than control or rgD$_2$t Alum treated groups.

In order to further evaluate the factors influencing the efficacy of prophylactic rgD$_2$t vaccines containing 3DMPL, a second set of experiments was initiated on larger guinea pig numbers.

Two antigen doses were compared (5 and 20 μg) and different adjuvant compositions were tested. Three immunizations were administered at days 0, 28 and 84. Animals were bled every two weeks for individual antibody determination by ELISA and neutralization assays. Vaginal washings were collected after the second immunization and were tested for the presence of systemic antibodies specific for rgD$_2$t.

Induction of Humoral Immunity

Results (Table 5) indicated that all the rgD$_2$t formulations containing 3D-MPL were able to stimulate high ELISA and neutralizing titers in the guinea pig sera.

The mean ELISA and neutralizing titers induced after three immunizations were very similar in the sera of groups vaccinated with a rgD$_2$t formulation containing either 5 μg or 20 μg gD$_2$t. There was no significant difference in the humoral response measured in the groups immunized with a rgD$_2$t Alum vaccine containing either 50 μg 3D-MPL (Group VI) or 100 mg 3D-MPL (Group X).

It is interesting to note that systemic anti-rgD2t antibodies (IgG class) could be detected in the vaginal washings of all vaccinated groups. This mucosally located anti-rgD$_2$t antibody response may play an important protective role by decreasing the load of infectious virus in the genital tract during primary infection.

Effect of Vaccination on HSV Primary Disease

Two weeks after the third immunization, guinea pigs were challenged intravaginally with HSV2. The effect of vaccination on the clinical and virological course of primary HSV2 infection is summarized in Table 6. As compared to the controls, animals vaccinated with a 5 μg rgD$_2$t Alum 3D-MPL formulation containing either 50 μg or 100 μg 3D-MPL (Groups VI and X) showed significantly (p<0.05) reduced skin lesion severity as well as reduction of skin lesions incidence.

Very similar results were observed in the group vaccinated with 5 μg rgD$_2$t in a 3D-MPL o/w emulsion (Group III). In the three vaccinated groups, very low viral replication could be detected in the vaginal swabs collected 5 days after the challenge.

Effect of Vaccination on HSV Recurrent Disease

Results are given in Table 6. As compared to the control groups, the incidence of skin lesions and the recurrence day number were significantly (p>0.05) reduced in the three vaccinated groups. These groups had also fewer recurrent episodes than control groups.

5. Conclusions

Results obtained in guinea pigs clearly show that vaccination with a rgD$_2$t formulation containing 3D-MPL delivered in an oil in water emulsion or combined with aluminium hydroxide is very effective in providing protection against primary and recurrent HSV2 disease when administered to guinea pigs prior to HSV2 inoculation. Such rgD$_2$t 3D-MPL formulations are able to improve specific humoral (neutralizing antibodies) and effector cell mediated (DTH) immune responses. These results are obtained using a low dose of rgD$_2$t (5 μg).

6. Immunogenicity of gD2t Formulations in Primates 6.1 Comparative Immunogenicity of rgD$_2$t/Alum and rgD$_2$t/Alum 3D-MPL Form The immunogenicity of rgD$_2$t/Alum and rgD$_2$t/Alum 3D-MPL vaccines were evaluated in cercopithecus aethiops (African Green Monkeys, AGM). Three immunizations were given at 0, 1 and 3 months. Specific humoral (ELISA and neutralizing titers) and effector cell mediated (DTH) immune responses were measured.

6.1.1. Experimental Procedure

Each formulation contained 20 mg rgD$_2$t and 0.5 mg equivalents AL$^{3+}$/dose. A dose of 50 μg 3D-MPL was used. Groups of cercopithecus aethiops (AGM) were immunized 3 times at days 0, 28 and 84. Immunizations were given intramuscularly in a 0.5 ml dose (20 rgD$_2$t). Animals were bled every ±2 weeks for antibody determination by ELISA and neutralization assays. The two formulations were also tested for their ability to induce T cell mediated immunity, as measured by the induction of delayed-type hypersensitivity (DTH) responses. Monkeys were given intradermally on the belly different rgD$_2$t doses (20, 5 and 1 μg) in saline 13 days after the second immunization. They were also skin tested with saline alone as control. Erythema and induration at site of intradermal injection were monitored 24 hrs and 48 hrs later.

6.1.2. Results a) Induction of Humoral Immunity

Before vaccination, none of the monkey sera showed any anti-HSV2 antibody activity (data not shown). As shown in table 7, both vaccines induced good ELISA and neutralizing titers after the second immunization. This antibody response was not boosted with a third immunization in the rgD$_2$t/Alum vaccinated monkeys. In contrast, monkeys receiving a third immunization with rgD$_2$t/Alum 3D-MPL produced increased ELISA and neutralizing antibody responses (mean ELISA titer: 10056; mean neutralizing titer: 950).

b) Induction of Effector T Cell Response (DTH)

Skin test results (table 8) showed that rgD$_2$t combined with Alum plus 3D-MPL was very potent in inducing an in vivo effector T cell response, in contrast to the rgD$_2$t Alum formulation. A strong DTH response was observed in all rgD$_2$t Alum 3D-MPL vaccinated animals skin tested with 20 mg rgD$_2$t. Specific DTH responses were also measured with the lower gD$_2$t concentrations (5 and 1g) in the majority of the monkeys (¾ for the 5 μg dose and ⅔ for the 1 μg dose). These rgD$_2$t doses induced weaker skin test responses than the 20 mg rgD$_2$t concentration.

6.2. Immunogenicity of rgD$_2$t/Alum 3D-MPL Formulations in Rhesus Monkeys

The immunogenicity of rgD$_2$t/Alum 3D-MPL vaccines containing different rgD$_2$t doses (100 μg, 10 μg, or 5 μg) was compared in rhesus monkeys.

6.2.1. Experimental Procedure

Each formulation contained 0.5 μg equivalents Al$^{3+}$ and 50 μg 3D-MPL per dose. Three groups of rhesus monkeys (4 monkeys/group) were immunized three times at days 0, 28 and 77, as follows:

Group 1: 100 μg rgD$_2$t Alum plus 3D-MPL (50 μg)

Group 2: 20 μg rgD$_2$t Alum plus 3D-MPL (50 μg)

Group 3: 5 μg rgD$_2$t Alum plus 3D-MPL (50 μg)

Immunizations were given intramuscularly in a 1 ml dose. Animals were bled every ±2 weeks for antibody determination by ELISA and neutralization assays.

6.2.2. Induction of Humoral Immunity

Before vaccination, none of the monkey sera showed any anti-HSV2 antibody activity. Good ELISA and neutralizing titers were observed in the three vaccinated groups receiving either 100, 20 and 5 mg gD$_2$t in Alum+3D-MPL. (Data not shown).

6.3. Conclusions

Results obtained in cercopithecus aethiops dearly indicate that a rgD$_2$t vaccine containing a combination of Alum with 3D-MPL significantly improve humoral (neutralizing antibodies) and effector cell mediated (DTH) specific immune responses. As compared to this vaccine, a rgD$_2$t Alum formulation is less potent in inducing neutralizing antibodies and is unable to induce an in vivo DTH response.

Results obtained in rhesus monkeys also show that a rgD$_2$t Alum+3D-MPL formulation is very effective in inducing a specific humoral response, even with low doses of antigen (5 μg or 20 μg rgD$_2$t).

7. General Conclusions

Results obtained in guinea pigs clearly indicate that adjuvant formulations containing either 3D-MPL delivered in an oil in water emulsion or combined with aluminium hydroxide are very effective in inducing a protective immune response with a recombinant HSV glycoprotein vaccine in the intravaginal guinea pig challenge animal model, even with very low doses of antigen (5 μg rgD$_2$t). Protection data also show that these rgD$_2$t 3D-MPL formulations are more potent in providing protection. Such 3D-MPL formulations are able to improve specific humoral (neutralizing antibodies) and effector cell mediated (DTH) immune responses.

Furthermore, the rgD$_2$t Alum 3D-MPL formulation was shown to also improve immunogenicity at the antibody level and to induce an effector T cell response in primates, suggesting that this adjuvant effect is not restricted to small animal species.

TABLE 1

Anti-HSV antibody response in sera of guinea pigs imunized with rgD$_2$t formulations before and after viral challenge.

| | Vaccine[1] | | Pre-challenge[2] | | Post-challenge[3] | |
|---|---|---|---|---|---|---|
| Group | Antigen | Adjuvant | ELISA titer | Neutralizing titer | ELISA titer | Neutralizing titer |
| 1 | rgD$_2$t | 3D-MPL o/w (R) | 81291 ± 20822 | 1600 | 68720 ± 24648 | 2200 ± 765 |
| 2 | rgD$_2$t | Alum 3D-MPL | 39897 ± 30165 | 2000 ± 800 | 27224 ± 13093 | 1800 ± 765 |
| 3 | rgD$_2$t | Alum | 20346 ± 23704 | 600 ± 400 | 28622 ± 24024 | 1333 ± 461 |
| 4 | — | Alum | <100 | <50 | 737 ± 878 | 142 ± 85 |
| 5 | — | 3D-MPL | <100 | <50 | 259 ± 244 | 1275 ± 1304 |
| 6 | untreated | — | <100 | <50 | 225 ± 194 | 119 ± 141 |

[1]rgD$_2$t dose = 5 μg. Animals were immunized three times at days 0, 28 and 95. They were challenged 2 weeks later with 10$^5$ pfu HSV2.
[2]Sera collected the day before challenge (= 14 days after the third immunization)
[3]Sera collected 2 weeks after challenge.
Values are given as arithmetic mean titers ± SD.

TABLE 2

Skin Test Results (DTH) in guinea pigs vaccinated with rgD$_2$t formulations.

| | Guinea Pig # | 24 hr reading | 48 hr reading | |
|---|---|---|---|---|
| Formulation | | E (mm) | E (mm) | E (mm) | I (mm) |
| rgD$_2$t 3D-MPL o/w (R) | 1 | 20 | 15 | 14 | 10 (N) |
| | 2 | 15 | 10 | 10 | 3 |
| | 3 | 20 | 17 (N) | 15 | 12 (N) |
| rgD$_2$t Alum 3D-MPL | 1 | 10 | 8 | 10 | 4 |
| | 2 | 15 | 12 | 12 | 3 |
| | 3 | 11 | 9 | 12 | 0 |
| Alum 3D-MPL | 1 | 0 | 0 | 0 | 0 |
| | 2 | 0 | 0 | 0 | 0 |
| | 3 | 0 | 0 | 0 | 0 |
| untreated | 1 | 0 | 0 | 0 | 0 |
| | 2 | 0 | 0 | 0 | 0 |

Guinea pigs were immunized at days 0 and 21 with 5 μg rgD$_2$t formulation (given intramuscularly). They were given intradermally 5 μg rgD$_2$t in saline at day 29. Skin test was read at 24 h and 48 h.
E = erythema at site of ID injection in millimeters.
I = induration at site of ID injection in millimeters.
N = necrosis at skin test site.

TABLE 3

Effect of immunization with rgD$_2$t formulations on the clinical and virological course of primary HSV2 infection in guinea pigs.

| Group | Vaccine[1] Antigen | Adjuvant | Incidence of Skin Lesions[2] | Skin Lesion Severity[3] | Vaginal Virus Titers[4] |
|---|---|---|---|---|---|
| 1 | rgD$_2$t | 3D-MPL o/w (R) | 0/4 | 0.1 ± 0.3 | 0 |
| 2 | rgD$_2$t | Alum 3D-MPL | 0/4 | 1 ± 0.4 | 6.25 ± 12.4 |
| 3 | rgD$_2$t | Alum | 3/4 | 4.4 ± 2.7 | 3575 ± 6010 |
| 4 | — | Alum | 5/5 | 6.2 ± 2.6 | 5216 ± 6295 |
| 5 | — | 3D-MPL | 4/5 | 5.1 ± 3.6 | 3298 ± 4475 |
| 6 | untreated | — | 7/8 | 7.3 ± 4.7 | 2214 ± 4519 |

[1]rgD$_2$t dose = 5 μg. Animals were immunized three times at days 0, 28 and 95. They were challenged 2 weeks later with 10$^5$ pfu HSV2.
[2]Number animals showing a lesion score ≧1 during the 12 days observation period
[3]Sum of the lesion scores (days 1–12), arithmetic mean ± SD
[4]Peak HSV titer (pfu/ml) in vaginal swabs collected 5 days post challenge.

TABLE 4

Effect of immunization with rgD$_2$t fomulations on the recurrent genital HSV2 disease in guinea pigs.

| Group | Vaccine (1) Antigen | Adjuvant | Incidence of Skin Lesions[2] | Episodes of recurrent disease[3] | Recurrence[4] days Numbers |
|---|---|---|---|---|---|
| 1 | rgD$_2$t | 3D-MPL o/w (R) | 1/4 | 1 ± 2 | 0.7 ± 1.5 |
| 2 | rgD$_2$t | Alum 3D-MPL | 2/4 | 1 ± 0.8 | 1.7 ± 3.5 |
| 3 | rgD$_2$t | Alum | 3/3 | 4.3 ± 1.5 | 8.3 ± 5 |
| 4 | — | Alum | 4/5 | 3.8 ± 3.3 | 7.6 ± 6.5 |
| 5 | — | 3D-MPL | 5/5 | 2.6 ± 1.1 | 6 ± 4.4 |
| 6 | untreated | — | 6/8 | 3.5 ± 2.2 | 9.9 ± 6 |

[1]rgD$_2$t dose 5 μg. Animals were immunized three times at days 0, 28 and 95. They were challenged 2 weeks later with 10$^5$ pfu HSV2.
[2]Number animals showing a lesion score ≧1 during the observation period (days 13–60)
[3]One recurrent episode is preceded and followed by a day without lesion and characterised by at least two days with erythema (score = 0.5) or one day with vesicle(s) (lesion score ≧1). Results expressed aa arithmetic mean ± SD (observation period: days 13–60).
[4]Total days animals experienced a recurrent herpetic episode, arithmetic mean ± SD (observation period: days 13–39).

TABLE 5

COMPARISON OF THE EFFECT OF DIFFERENT ADJUVANT FORMULATIONS ON THE IMMUNOGENICITY OF rgD2t IN GUINEA PIGS

| | rgD2t VACCINE[1] | | Anti-HSV antibody response after two immunisations | | | Anti HSV antibody response after three immunizations - prechallenge titer[3] | |
|---|---|---|---|---|---|---|---|
| | | | IN SERA | | IN VAGINAL[5] | IN SERA[4] | |
| GROUP | dose | Adjuvant | Elisa titer | Neutral titer | WASHINGS | Elisa titer | Neutral titer |
| I | 20 μg | 3DMPL (50 μg) o/w (R) | 31462 ± 9087 | 850 ± 396 | 0.780 ± 0.376 | 19958 ± 10171 | 3400 ± 1994 |
| II | 5 μg | 3DMPL (50 μg) o/w (R) | 35015 ± 14395 | 412 ± 264 | 1.000 ± 0.177 | 51688 ± 40120 | 4342 ± 2879 |
| III | 20 μg | 3DMPL (50 μg) o/w (S) | 16720 ± 12641 | 1380 ± 758 | 0.700 ± 0.232 | 36647 ± 24126 | 4080 ± 2883 |
| IV | 5 μg | 3DMPL (50 μg) o/w (S) | 14992 ± 9885 | 840 ± 571 | 0.570 ± 0.200 | 45082 ± 24221 | 4560 ± 2502 |
| V | 20 μg | Alum 3DMPL (50 μg) | 14452 ± 7476 | 740 ± 499 | 0.620 ± 0.175 | 16015 ± 7846 | 3280 ± 2276 |
| VI | 5 μg | Alum 3DMPL (50 μg) | 10174 ± 4219 | 420 ± 301 | 0.520 ± 0.175 | 20488 ± 9562 | 2640 ± 1510 |
| VII | — | Alum 3DMPL (50 μg) | <100 | <50 | <0.020 | <100 | <50 |
| VIII | — | 3DMPL (50 μg) o/w (R) | <100 | <50 | <0.020 | <100 | <50 |
| IX | — | untreated | <100 | <50 | <0.020 | <100 | <50 |
| X | 5 μg | Alum 3DMPL (100 μg) | 4602 ± 3953 | 163 ± 151 | 0.671 ± 1.187 | 16588 ± 6945 | 2560 ± 1678 |

[1]Animals were immunized three times at days 0, 28 and 64. They were challenged 2 weeks later with 10$^5$ pfu HSV2.
[2]Sera and vaginal washings collected 14 days after the second immunization.
[3]Sera collected the day before challenge (= 14 days after the third immunization).
[4]Values are given as arithmetic mean titers ± SD
[5]Corresponds to the optical density (at 492 nm) per 0.5 μg/ml total IgG measured in the standard anti-gD2t ELISA assay, arithmetic mean ± SD.

TABLE 6

EFFECT OF IMMUNIZATION WITH rgD2t FORMULATIONS ON THE CLINICAL AND VIROLOGICAL COURSE OF HSV2 INFECTION IN GUINEA PIGS

| | VACCINE | | | |
|---|---|---|---|---|
| | 5 μpg rgD2t 3DMPL o/w (s) Group III | 5 μg rgD2t Alum 3DMPL (50 μg) Group VI | 5 μg rgD2t Alum 3DMPL (100 μg) Group X | CONTROLS Groups VII - VIII - IX |
| PRIMARY HSV2 INFFECTION | | | | |
| Incidence of skin lesions (%) | 1/9  11% | 1/10  10% | 0/10  0% | 12/14  86% |
| Skin lesion severity | 1.2 ± 1 | 0.7 ± 0.7 | 0.9 ± 1 | 8.6 ± 5.1 |
| Vaginal virus titers (pfu/ml) | 0 | 0 | 1.5 ± 4.7 | 1077 ± 1682 |
| RECURRENT HSV2 INFFCTION | | | | |
| Incidence of skin lesions (%) | 2/9  22% | 2/10  20% | 3/10  30% | 11/14  79% |
| Recurrence day number | ' 1 ± 2.3 | 1.6 ± 2.1 | 1.6 ± 2.7 | 7.3 ± 6 |
| Recurrence episode number | 0.2 ± 0.4 | 0.6 ± 0.7 | 0.5 ± 0.8 | 1.9 ± 1.2 |

Experimental schedule: 3 immunizations at days 0, 28 and 84.
Challenge 2 weeks after the last immunization with $10^5$ pfu HSV2.
Primary HSV2 infection: (observation period days 4 to 12 post challenge)
Incidence of skin lesions (%): number of animals with vesicle(s) (lesion score $\geq 1$)
Skin lesion severity: sum of the lesion scores (for the days 4 to 12), arithmetic mean ± SD
Vaginal virus tiiers: virus titers (pfu/ml) in vaginal swabs collected 5 days after the challenge
Recurrent HSV2 infection: (observation period days 13 to 39 post challenge)
Incidence of skin lesions (%): number (%) of animals with vesicle(s) (lesion score $\geq 1$)
Recurrence day number: total days animals experienced a recurrent herpetic disease, arithmetic mean ± SD.
Animals were scored positive for recurrent disease either if a 0.5 lesion score (erythema) was recorded for 2 successive days at least or if a lesion score $\geq 1$ (vesicle(s)) was observed at any day.
Recurrence episode number: arithmetic mean, ± SD

TABLE 7

DTH RESULTS IN AFRICAN GREEN MONKEYS VACCINATED WITH GD2T ALUM OR GD2T ALUM 3D MPL

| | | 24 h reading | | | | 48 h reading | | | |
|---|---|---|---|---|---|---|---|---|---|
| VACCINE | MONKEY NB | PBS | gD2t 1 μg | gD2t 5 μg | gD2t 20 μg | PBS | gD2t 1 μg | gD2t 5 μg | gD2t 20 μg |
| gD2t | JO358 | — | ND | — | — | — | ND | — | — |
| ALUM | JO359 | — | ND | — | — | — | ND | — | — |
| | JO363 | — | ND | — | — | — | ND | — | — |
| | JO364 | — | ND | — | — | — | ND | — | — |
| | JO366 | — | ND | — | — | — | ND | — | — |
| gD2t | JO348 | — | — | E | I 2-4 | — | — | I | I |
| ALUM | JO349 | — | E 1-2 | I 5-8 | cm | — | E | I | I |
| 3D MPL | JO375 | — | mm | mm | E 7-9 | — | E | I | I |
| | JO515 | — | E 1-2 | I 3-4 | mm | — | — | — | Eweak |
| | | | mm | mm | I 4-6 | | | | |
| | | | — | — | mm E | | | | |
| CONTROLS | JO320 | — | — | — | — | — | — | — | — |
| | JS110 | — | — | — | — | — | — | — | — |

Monkeys were immunized at days 0 and 28 with 20 μg gD2t formulation (given intramuscularly). They were given intradermally in the belly different gD2t doses in saline 13 days later. Skin test was read at 24 h and 48 h.
E: erythema at site of ID injection
I: induration at site of ID injection
ND = not done

TABLE 8

COMPARATIVE IMMUNOGENICITY OF GD2T ALUM AND GD2T ALUM 3D MPL
FORMULATIONS IN AFRICAN GREEN MONKEYS: SEROLOGICAL RESPONSES

| VACCINE* | MONKEY NB | Post II | | | | | Post III | |
|---|---|---|---|---|---|---|---|---|
| | | 14 days | | 28 days | 56 days | | 14 days | |
| | | ELISA TITER | NEUT TITER | ELISA TITER | ELISA TITER | NEUT TITER | ELISA TITER | NEUT TITER |
| gD2t ALUM | JO358 | 1388 | 400 | 6572 | 1135 | 200 | 2050 | 400 |
| | JO359 | 4731 | 400 | 3232 | 1866 | 100 | 2110 | 200 |
| | JO363 | 1376 | 200 | 2316 | 1300 | 50 | 1205 | 50 |
| | JO364 | 5914 | 1600 | 5275 | 3740 | 400 | 6323 | 800 |
| | JO366 | 21104 | 400 | 3696 | 2550 | 200 | 2302 | 200 |
| | Arit mean ± SD | 6902 ± 8190 | 600 ± 565 | 4218 ± 1697 | 2118 ± 1062 | 190 ± 134 | 2796 ± 2915 | 330 ± 290 |
| gD2t ALUM/ 3DMPL | JO348 | 7120 | 200 | 10175 | 4490 | 200 | 11082 | 400 |
| | JO349 | 14437 | 1600 | 15409 | 7361 | 800 | 15848 | 1600 |
| | JO375 | 7990 | 800 | 5170 | 2953 | 800 | 6797 | 1600 |
| | JO515 | 6515 | 200 | 7246 | 3660 | 100 | 6497 | 200 |
| | Arit mean ± SD | 9015 ± 3664 | 700 ± 663 | 9500 ± 4442 | 4616 ± 1934 | 475 ± 377 | 10056 ± 4392 | 950 ± 754 |

*Each vaccine dose contains 20 pg gD2t
ELISA titer = midpoint titer
NEUT titer = reciprocal of the highest serum dilution giving 100% protection against the cytopathogen effect

We claim:

1. A vaccine formulation comprising a Herpes Simplex Virus glycoprotein D or an immunological fragment of the Herpes Simplex Virus glycoprotein D, 3 Deacylated monophosphoryl lipid A and a carrier selected from the group consisting of alum and an oil in water emulsion and wherein the vaccine formulation in vivo induces neutralizing antibodies and cellular immunity mediated through T cells.

2. A vaccine formulation as claimed in claim 1 wherein the glycoprotein D is a Herpes Simplex Virus 2 glycoprotein D or immunological fragment of the Herpes Simplex Virus 2 glycoprotein D.

3. A vaccine formulation as claimed in claim 1 wherein the glycoprotein D is a truncated protein.

4. A vaccine formulation as claimed in claim 2 wherein the glycoprotein D is a truncated protein.

5. A vaccine formulation as claimed in claim 4 wherein the truncated glycoprotein D is devoid of the C terminal anchor region.

6. A vaccine formulation as claimed in claim 5 wherein the truncated glycoprotein D is a genetically engineered recombinant truncated glycoprotein D produced in transfected ChineseHamster Ovary cells herein designated HSVrgD$_2$t.

7. A vaccine formulation as claimed in claim 1 wherein the glycoprotein D is conjugated to a particulate carrier.

8. A vaccine formulation as claimed in claim 1 wherein 3 Deacylated monophosphoryl lipid A is present in the range of 10 μg–100 μg per dose.

9. A vaccine formulation comprising 3 Deacylated monophosphoryl lipid A in the range of 10 μg–100 μg per doses, the Herpes Simplex Virus 2 glycoprotein D wherein said glycoprotein D is devoid of a transmembrane domain and a carrier selected from the group consisting of alum and an oil in water emulsion.

10. A method of treating a human subject suffering from or susceptible to Herpes Simplex Virus infections comprising administering an effective amount of a vaccine according to claim 1.

11. A method of producing a vaccine according to claim 1 wherein the method comprises mixing the Herpes Simplex Virus glycoprotein D or an immunological fragment of the Herpes Simplex Virus glycoprotein D with a carrier and 3 Deacylated monophosphoryl lipid A, and recovering the resulting mixture.

* * * * *